(12) United States Patent
Schroff et al.

(10) Patent No.: US 10,006,032 B2
(45) Date of Patent: Jun. 26, 2018

(54) PREDICTIVE BIOMARKER FOR CANCER THERAPY

(71) Applicant: Mologen AG, Berlin (DE)

(72) Inventors: Matthias Schroff, Berlin (DE); Manuel Schmidt, Berlin (DE); Kerstin Kapp, Berlin (DE); Burghardt Wittig, Berlin (DE)

(73) Assignee: Mologen AG, Berlin (DE)

( * ) Notice: Subject to any disclaimer, the term of this patent is extended or adjusted under 35 U.S.C. 154(b) by 0 days. days.

(21) Appl. No.: 14/891,869

(22) PCT Filed: May 15, 2014

(86) PCT No.: PCT/EP2014/059995
§ 371 (c)(1),
(2) Date: Nov. 17, 2015

(87) PCT Pub. No.: WO2014/191222
PCT Pub. Date: Apr. 12, 2014

(65) Prior Publication Data
US 2016/0115479 A1 Apr. 28, 2016

(30) Foreign Application Priority Data
May 30, 2013 (GB) .................................. 1309657.3

(51) Int. Cl.
| | |
|---|---|
| C12N 15/117 | (2010.01) |
| G01N 33/50 | (2006.01) |
| G01N 33/574 | (2006.01) |
| A61K 39/39 | (2006.01) |

(52) U.S. Cl.
CPC ............ *C12N 15/117* (2013.01); *A61K 39/39* (2013.01); *G01N 33/5091* (2013.01); *G01N 33/574* (2013.01); *C12N 2310/17* (2013.01); *C12N 2310/531* (2013.01); *C12N 2320/30* (2013.01); *G01N 2333/7051* (2013.01); *G01N 2333/70503* (2013.01); *G01N 2333/70596* (2013.01); *G01N 2469/00* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2008/0254045 A1* | 10/2008 | Donda ................. | A61K 39/385 424/178.1 |
| 2009/0053250 A1 | 2/2009 | Wittig et al. | |
| 2009/0220931 A1 | 9/2009 | Schmidt et al. | |
| 2012/0128699 A1 | 5/2012 | Kandimalla et al. | |

FOREIGN PATENT DOCUMENTS

| | | | |
|---|---|---|---|
| EP | 2073009 A1 * | 6/2009 | ......... G01N 33/5094 |
| JP | 2011-519847 A | 7/2011 | |
| WO | 2009/023819 A1 | 2/2009 | |
| WO | 2009/133378 A2 | 11/2009 | |
| WO | 2010/055340 A1 | 5/2010 | |

OTHER PUBLICATIONS

Hans-Joachim Schmoll et al., "Maintenance treatment with the immunomodulator MGNI 703, a Toll-like receptor 9 (TLR9) agonist, in patients with metastatic colorectal carcinoma and desease control after chemotherapy: a randomised, double-blind, placebo-controlled trial," Journal of cancer research and clinical oncology, May 10, 2014.
H.-J. Schmoll et al, Updated results of the randomized phase 2 impact trial: maintenance with TLR-9 agonist MGNI 703 vs placebo in patients with metastatic colorectal carcinoma (MCRC); Annals of oncology, vol. 24, No. suppl 4, Jun. 1, 2013, pp. iv16-iv17.
Riera Knorrenschild et al. "Maintenance with the TLR-9 agonist MGNI 703 versus placebo in patients with advanced colorectal camincoma (mCrC): A randomized phase II trial (impact)," ASCO Meeting abstracts; May 30, 2013.
Varghese et al., "A novel iNKT-mediated T cell exhaustion in cancer," 188 (1001):165.13; The Journal of Immunology; Jan. 1, 2012.
Montoya C J et al., "Increades IFN-gamma production by NK and CD3+/CD56+ cells in sexually HIV-1-exposed but uninfected individuals; Clinical Immunology," Academic Press; US vol. 120, No. 2; Aug. 1, 2006, pp. 138-146.
J. Vas et al, "Regulatory Roles for NKT Cell Ligands in Environmentalle induced autoimmunity," The Journal of mmunology, vol. 181, No. 10, 3. Nov. 2008, pp. 6779-6788.
Hui Guo et al., "High Frequency of activated killer and natural killer T-cells in patients with new onset of type 2 diabetes mellitus," Society for experimental biology and medicine; vol. 237, 2012, pp. 556-562.
Carvaljo, K.I et al., "Stewed Distribution of Circulating Activated Natural Killer T (NKT) Cells in Patients with Common variable Immunodeficiency Disorders (CVID)," PLoS one, vol. 5, 2010.
Raveendra R. Kulkarni, "Costimulatory activation of murine invariant natural killer T cells by toll-like receptor agonists," Cellular Immunology, vol. 277,, 2012, pp. 33-43.
Moreno M. et al., "Differential indirect activation of human invariant natural killer T cells by toll-like receptor agonists," Immunotherapy, vol. 1, 2009, pp. 557-570.
Mario Moreno et al., "Toll-like receptor agonists and invariant natural killer T-cells enhance antibody-dependent cell-mediated cytotoxicity (ADCC)," Cancer Letters, vol. 272, 2008, pp. 70-76.
Lan Wu et al: "Natural Killer T Cells and autoimmune Desease"; Current Molecular Medicine 2009, vol. 9, No. 1, pp. 4-14.
Oren A et al; A" comparative study of immunomagnetic methods used for separation of human natural killer cells from peripheral blood," Journal of Immunological Methods 303 (2005), 1-10.
Gitte S. Jensen et al, "Immunomodulation by SanPharma Fungal Metabolic Products," Journal of Alternative and Complementary Medicine, vol. 12, No. 4 ,pp. 409-416 (2006).
Varghese et al., "A novel iNKT-mediated vaccine maneuver overcomes PD-1-mediated T cell exhaustion in cancer (165.13)," The Journal of Immunology, vol. 188 (1 Supplement), No. 165.13, May 1, 2012. (4 pages total).

(Continued)

*Primary Examiner* — Addison D Ault
(74) *Attorney, Agent, or Firm* — Sughrue Mion, PLLC

(57) ABSTRACT

The present invention relates generally to the identification of patients suffering from cancer whether they will respond to specific therapies. More particularly the invention relates to a method and means for identifying responder to a therapy TLR-9 agonists.

6 Claims, 5 Drawing Sheets

(56) References Cited

OTHER PUBLICATIONS

Communication, dated Dec. 8, 2017, issued by the Intellectual Property Office of Canada in counterpart Canadian Application No. 2,907,980.

Friedberg Jet al., "Phase II study of a TLR-9 agonist (1018 ISS) with rituximab in patients with relapsed or refractory follicular lymphoma.", British Journal of Haematolgy, 146 (3):pp. 282-291, Aug. 2009.

Tarhini et al., "Differing Patterns of Circulating Regulatory T-Cells and Myeloid Derived Suppressor Cells in Metastatic Melanoma Patients Receiving Anti-CTLA4 Antibody and Interferon-α or TLR-9 Agonist and GM-CSF with Peptide Vaccination", J Immunother. vol. 35, No. 9, pp. 702-710, Nov. 2012.

King et al., "Natural killer cells and CD56+ T cells in the blood of multiple myeloma patients: analysis by 4-colour flow cytometry.", Cytometry. 26(2), pp. 121-124, Jun. 15, 1996.

Schmidt et al., "87. First Results of a Phase 2-3 Clinical Study with the Immunomodulator MGN1703 in Patients with Advanced Colorectal Carcinoma (Impact Study)", Molecular Therapy, vol. 19, S35, May 2011.

Translation of the communication dated Jan. 17, 2017, issued by the Japanese Patent Office in counterpart Japanese Application No. 2016-515715.

Translation of the communication dated Nov. 29, 2017, issued by the Japanese Patent Office in counterpart Japanese Application No. 2016-51 5715.

Zdrazilova-Dubska et al., "NKT-like Cells are Expanded in Solid Tumour Patients", Klin Onkol, vol. 25(Suppl 2), 2012, pp. 2S21-2S25. (5 pages total).

English Translation of the Communication, dated Jun. 8, 2017, issued by the Russian Patent Office in counterpart Russian Application No. 2015150739/15.

* cited by examiner

PREDICTIVE BIOMARKER FOR CANCER THERAPY

FIELD OF THE INVENTION

The present invention relates generally to the identification of cancer patients as to whether they will respond to specific therapies. More particularly the invention relates to a method and DNA construct for identifying responders to a therapy involving immune activating DNA constructs, as well as to a DNA construct intended to treat cancer patients individually characterized as potential responders prior to the start of a treatment with said construct.

BACKGROUND OF THE INVENTION

Biomarkers are substances found in blood or other body fluids, in tissues or as receptors on cells that signal the presence or absence of a condition or disease, like cancer for instance. Biomarkers can be differentiated into predictive, prognostic and pharmacodynamics biomarkers.

Predictive biomarkers are used to assess the probability that a patient will respond to or benefit from a particular treatment. Prognostic biomarkers allow for the classification of tumours with regard to their aggressive potential to guide a decision of whom to treat or how aggressively to treat. Pharmacodynamic biomarkers measure the near-term treatment effects of a drug on the tumour and might be used to guide dose selection during clinical development of a new anti-cancer drug.

Targeted therapies are treatments that work on a molecular level to stop a cancer from growing or spreading. In order to avoid unnecessary approaches, because such therapies are usually related to the use of very aggressive drugs, there is a need for tools allowing to predict whether a patient will respond to a targeted therapy or not.

With regards to the fact that therapies become more and more target specific, the role of biomarkers will increase. They will help to individualise therapeutic approaches and to open the way to individualised oncology. Even the possibility to distinguish a responder to a specific therapy from a non-responder will help to prevent that patients will be subject to unnecessary treatments.

A commonly known and well-approved treatment of cancer is chemotherapy. One major disadvantage of chemotherapy is the use of very aggressive pharmaceuticals causing severe side effects. In order to minimize these side effects many attempts have been undertaken to minimize dosage of chemotherapeutics like for instance combining chemotherapy with immune activating agents. One approach is the use of immune activating DNA.

So-called unmethylated CG sequences have been shown to activate the immune system very effectively (Krieg A M, Yi A K, Matson S, Waldschmidt T J, Bishop G A, Teasdale R, Koretzky G A, Klinman D M; CpG motifs in bacterial DNA trigger direct B-cell activation; Nature 1995 Apr. 6 374:6522 546-9). Those sequences are derived from bacteria. EP 1 196 178 discloses a covalently closed circular DNA with partially self-complementary sequences resulting in a DNA construct having a double stranded stem with single stranded loops at both ends comprising the unmethylated CG motifs.

The combination of the dumbbell-shaped DNA constructs of EP 1 196 178 with chemotherapeutics to treat cancerous diseases has been proposed by EP 1 776 124. Patients who were treated with the DNA constructs of EP 1 196 178 received subsequently chemotherapeutic. It turned out that the amount of chemotherapeutic could be reduced by the disclosed combination. But this document does not disclose information about tools for identifying whether a patient will respond to the application of the combination therapy at all.

It is an object of the present invention to provide a method for predicting whether a cancer patient will respond to the treatment with immune activating DNA. Another object of the invention is the immune activating DNA itself, which can be used in such a method, i.e. to treat a patient identified as responder prior to the start of treatment

BRIEF SUMMARY OF THE INVENTION

The present invention provides a method for predicting or monitoring whether a patient suffering from cancer or an autoimmune disease will respond or responds to treatment with a TLR-9 agonist by determining the frequency of activated natural killer T (NKT) cells. It is preferred to determine the cluster of differentiation or cluster of designation (CD) molecules CD3+/CD56+/CD69+ for immunophenotyping of activated NKT cells. The ratio of activated NKT cells of the whole NKT cell population may also be determined in order to assess the probability whether a patient will respond to a treatment with a TLR-9 agonist.

It is intended that the TLR-9 agonist is a DNA construct comprising at least one sequence motif $N^1N^2CGN^3N^4$, wherein $N^1N^2$ and $N^3N^4$ is any combination of A, C, T, and G, and C is deoxycytidine, G is deoxyguanosine, A is deoxyadenosine and T is deoxythymidine A responder to the treatment with the TLR-9 agonist shall have a frequency of at least 3% of activated NKT cells of the whole NKT cell population.

It is further intended that previously an induction therapy with a non-DNA drug may be performed. Such a therapy comprises chemotherapy with or without angiogenesis inhibitor or the use of antibodies.

A further object of the present disclosure is a TLR-9 agonist for use in a method of treatment of cancer, characterised in that the patient has elevated levels of activated NKT cells.

It is intended that the used TLR-9 agonist comprises at least a DNA construct comprising at least one sequence motif $N^1N^2CGN^3N^4$, wherein $N^1N^2$ and $N^3N^4$ is any combination of A, C, T, and G, and C is deoxycytidine, G is deoxyguanosine, A is deoxyadenosine and T is deoxythymidine. The agonist may further be characterised by $N^1N^2$ being an element selected from the group comprising GT, GG, GA, AT or AA, $N^3N^4$ being an element selected from the group comprising CT or TT.

The agonist may comprise DNA that is a linear open-chained DNA construct comprising single or double-stranded DNA or is a linear double-stranded DNA construct, which comprises at least one end with a single stranded loop. Instead of using loops to protect the ends of the linear double strands at least one L-DNA nucleotide may be used as part of the DNA double strand.

The sequence motif $N^1N^2CGN^3N^4$ shall be located within a single-stranded and/or a double-stranded region of the DNA sequence. It is further intended that at least one nucleotide of a DNA TLR-9 agonist is modified with a functional group selected from the group comprising carboxyl, amine, amide, aldimine, ketal, acetal, ester, ether, disulfide, thiol and aldehyde groups.

The agonist comprising a DNA construct can be linked to a compound selected from the group comprising peptides, proteins, carbohydrates, antibodies, lipids, micelles, vesicles, synthetic molecules, polymers, micro projectiles, metal particles, nanoparticles, or a solid phase.

It is further intended that the agonist comprising a DNA construct can be part of a pharmaceutical composition, wherein the pharmaceutical composition can be a vaccine.

Another object of the present disclosure is a kit for predicting or monitoring whether a patient suffering from cancer or auto immune disease will respond or responds to treatment with a TLR-9 agonist comprising means for detecting and quantifying the frequency of activated NKT cells of the whole NKT cell population.

It is intended for the kit that the TLR-9 agonist may comprise a DNA construct comprising at least one sequence motif $N^1N^2CGN^3N^4$, wherein $N^1N^2$ and $N^3N^4$ is any combination of A, C, T, and G, and C is deoxycytidine, G is deoxyguanosine, A is deoxyadenosine and T is deoxythymidine

DETAILED DESCRIPTION OF THE INVENTION

Figure 1:
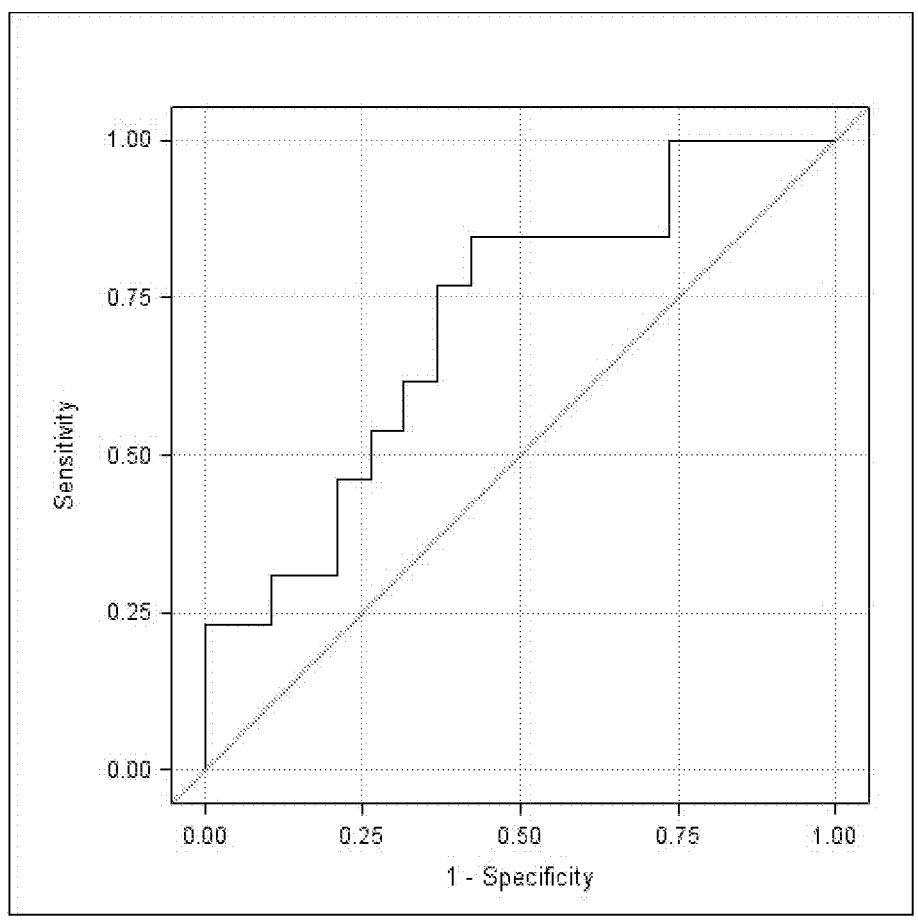
FIG. 1: ROC curves in verum patients for activated NKT cells.

Within the meaning of the present invention MGN1703 designates a DNA construct of a covalently closed partially self-complementary DNA chain having a double stranded stem and single stranded terminal loops bearing unmethylated CG motifs.

A "stem" according to the present disclosure shall be understood as a DNA double strand formed by base pairing either within the same DNA molecule (which is then partially self-complementary) or within different DNA molecules (which are partially or completely complementary). Intramolecular base pairing designates base pairing within the same molecules, and base pairing between different DNA molecules is termed as intermolecular base-pairing.

A "loop" within the meaning of the present disclosure shall be understood as an unpaired, single-stranded region either within or at the end of a stem structure. A "hairpin" is a distinct combination of a stem and a loop, which occurs when two self-complementary regions of the same DNA molecule hybridize to form a stem with an unpaired loop.

A "dumbbell-shape" describes a linear DNA construct with hairpins at both ends flanking a stem region. Thus, a "linear DNA construct" within the context of the present disclosure describes a linear dumbbell-shaped DNA construct comprising single stranded loops at both ends of a double stranded DNA stem.

Immunomodulation according to the present disclosure refers to immune activation and immunosuppression. Immune activation means preferentially that effector cells of the immune system are activated in order to proliferate, migrate, differentiate or become active in any other form. B cell proliferation for instance can be induced without co-stimulatory signals by immune activating DNA molecules, which normally require a co-stimulatory signal from helper T-cells.

Immunosuppression on the other hand shall be understood as reducing the activation or efficacy of the immune system. Immunosuppression is generally deliberately induced to prevent for instance the rejection of a transplanted organ, to treat graft-versus-host disease after a bone marrow transplant, or for the treatment of autoimmune diseases such as, for example, rheumatoid arthritis or Crohn's disease.

In this context, immunomodulation may also refer to influencing the nature or the character of an immune reaction, either by affecting an immune reaction, which is still developing or maturing or by modulating the character of an established immune reaction.

The term "vaccination" used in this disclosure refers to the administration of antigenic material (a vaccine) to produce immunity to a disease. Vaccines can prevent or ameliorate the effects of infection by many pathogens such as viruses, fungi, protozoan parasites, bacteria but also of allergic diseases and asthma, as well as of tumors. Vaccines typically contain one or more adjuvants, e g immune activating nucleic acids, used to boost the immune response. Vaccination is generally considered to be the most effective and cost-effective method of preventing infectious and other diseases.

The material administered can, for example, be live but weakened forms of pathogens (bacteria or viruses), killed or inactivated forms of these pathogens, purified material such as proteins, nucleic acids encoding antigens, or cells such as tumor cells or dendritic cells. In particular, DNA vaccination has recently been developed. DNA vaccination works by insertion (and expression, triggering immune system recognition) of DNA encoding antigens into human or animal cells. Some cells of the immune system that recognize the proteins expressed will mount an attack against these proteins and against cells expressing them. One advantage of DNA vaccines is that they are very easy to produce and store. In addition, DNA vaccines have a number of advantages over conventional vaccines, including the ability to induce a wider range of immune response types.

Vaccination can be used as a prophylactic approach, leading to immunity against the antigen in the vaccinated, healthy individual upon exposure to the antigen. Alternatively, a therapeutic vaccination can cause an improved response of the immune system of the vaccinated, diseased individual, by guiding the immune system of the individual towards the antigens. Both prophylactic and therapeutic vaccination can be applied to humans as well as animals.

The term "cancer" comprises cancerous diseases or a tumor being treated or prevented that is selected from the group comprising, but not limited to, mammary carcinomas, melanoma, skin neoplasms, lymphoma, leukemia, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

Autoimmune diseases according to the present disclosure comprise rheumatoid arthritis, Crohn's disease, systemic lupus (SLE), autoimmune thyroiditis, Hashimoto's thyroiditis, multiple sclerosis, Graves' disease, myasthenia gravis, celiac disease and Addison's disease.

During experiments with immune activating dumbbell-shaped DNA constructs with unmethylated CG sequences in the single-stranded terminal loops it turned out that elevated frequencies of certain cell types of the immune activation and effector pathway were related to a successful therapy with the DNA constructs.

In vertebrates, the so-called "toll-like receptors" (TLRs) are part of the innate immune system. TLRs are a family of specialized immune receptors that induce protective immune responses when they detect highly conserved pathogen-related molecular patterns, such as proteins, lipid structures, sacharidic structures, and certain nucleic acids. Synthetic agonists for several TLRs, including TLR-3, TLR-4, TLR-7, TLR-8, and TLR-9, have been or are being developed for the treatment of cancer, generally with the intention to activate the immune system in the presence of tumours. TLR-9 recognizes the presence of unmethylated CG-containing DNA sequences, which are typically found in bacteria, but practically never in human genomic DNA. Thus, unmethylated CG-containing DNA sequences have been designed as artificial TLR-9 agonists. The effect of such unmethylated CG-containing DNA constructs depends on their interaction with TLR-9, and DNA-protein interaction depends on the conformation of both DNA and protein. Experimental data demonstrate that dumbbell-shaped DNA molecules are surprisingly suitable for the induction of an immune response.

In order to identify a tool for predicting whether a cancer patient will respond to the application of a TLR-9 agonist, a dumbbell-shape DNA construct having unmethylated CG motifs in the single stranded terminal loops was used.

In total, 46 patients suffering from metastatic colorectal cancer who had previously been treated for 4.5 to 6 month in a standard first-line combination therapy with or without a human monoclonal antibody inhibiting vascular endothelial growth factor A were selected for the study. After a treatment-free interval of ca. 1-6 weeks, a randomization of the patients was performed, so that 32 patients received 60 mg per dose of the DNA construct MGN1703 and 14 patients received a placebo, each patient twice weekly by subcutaneous injection.

After 12 weeks of treatment, all patients were examined for tumour-progression. Based on the presence or absence of tumour progression, patients were divided into two groups, designated as "PFS groups". Patients whose tumour had not progressed were designated as progression-free patients and labelled "PFS1", whiles patients with tumour progression were labelled as "PFS0". Obviously, a lack of tumour progression (PFS1) indicates a possible response to the treatment, while tumour growth (PFS2) indicates a lack of response. Treatment was continued for each patient until tumour progression was found.

Table 1 summarizes the results. It is obvious that nearly all progression-free patients received the DNA construct.

TABLE 1

Designation of patients

| Treatment arms | Group designation | | Total |
| --- | --- | --- | --- |
| | PFS0 | PFS1 | |
| MGN1703 | 19 | 13 | 32 |
| Placebo | 13 | 1 | 14 |
| Total | 32 | 14 | 46 |

Prior to the first application of MGN1703 or placebo (at baseline) blood samples of all patients were collected. The distribution of the following immunovariables, e.g. part of whole PBMC population and relation of activated and non-activated sub populations was determined A correlation of the respective PFS group designation after 12 weeks and all immunovariables at baseline was investigated. The following immunovariables were determined: monocytes, activated monocytes 1, activated monocytes 2, B-Cells, activated B-cells, T-cells, activated T-cells, natural killer (NK)-cells, activated NK-cells, NKT-cells, activated NKT-cells, plasmacytoid dendritic cells (pDCs), activated pDCs, myeloid dendritic cells (mDCs), and activated mDCs. Table 2 summarizes the context of cell types, CDs and the determined frequencies.

TABLE 2

Relation of cell types, CDs and determined frequencies

| Cell Type | Identified by | Frequency as percentage of |
| --- | --- | --- |
| monocytes | CD14+ | all PBMCs |
| activated monocytes 1 | CD14+/CD86+ | all monocytes |
| activated monocytes 2 | CD14+/CD169+ | all monocytes |
| B-cells | CD19+ | all PBMCs |
| activated B-cells | CD19+/CD86+ | all B-cells |
| T-cells | CD3+/CD56− | all PBMCs |
| activated T-cells | CD3+/CD56−/CD69+ | all T-cells |
| natural killer (NK-)cells | CD3−/CD56+ | all PBMCs |
| activated NK-cells | CD3−/CD56+/CD69+ | all natural killer cells |
| NKT cells | CD3+/CD56+ | all PBMCs |
| activated NKT cells | CD3+/CD56+/CD69+ | all NKT cells |
| plasmacytoid dendritic cells (pDCs) | Lin1−/CD123+/HLA-DR+ | all PBMCs |
| activated pDCs | Lin1−/CD123+/HLA-DR+/CD40+ | all pDCs |
| myeloid dendritic cells (mDCs) | Lin1−/CD11c+/HLA-DR+ | all PBMCs |
| activated mDCs | Lin1−/CD11c+/HLA-DR+/CD86+ | all mDCs |

To assess whether one of the immunovariables may serve as a proper biomarker, a so-called Cox regression was calculated for each immunovariable. A Cox regression allows estimating the effect of parameter(s) without any consideration of the hazard function. The resulting hazard ratio from such a calculation should be below 1 and related to a significant p value being below 0.05. Otherwise the observed effect would not be related to the applied TLR-9 agonist. Those criteria applied only to activated NKT cells having a hazard ratio of about 0.933 and a p value of 0.0309.

Surprisingly, the percentage of activated NKT cells could be used to predict treatment success within the verum group. The relationship between the percentage of activated NKT cells and the PFS group status was studied using advanced, well-established statistical analyses within the verum group.

A receiver operating characteristic (ROC) curve, or simply ROC curve, shows the performance of a binary classifier system as its discrimination threshold is varied. ROC curves are created by plotting the fraction of true positives out of the positives versus the fraction of false positives out of the negatives at various threshold settings. The true positives are also designated as sensitivity and the false positives is one minus the specificity or true negative rate.

ROC analysis is used in medicine, radiology, biometrics, and other areas for many decades and is increasingly used in machine learning and data mining research. In biomarkers, it can be used to study the study whether a potential biomarker can have clinical validity, i.e., whether it can be used for predictive purposes. A successful diagnostic test or biomarker will result in a curve that bends above the diagonal while an unsuccessful test will mirror the diagonal, or fall below it. Thus, a ROC curve provides information whether a diagnostic test is successful or not.

Figure 2:
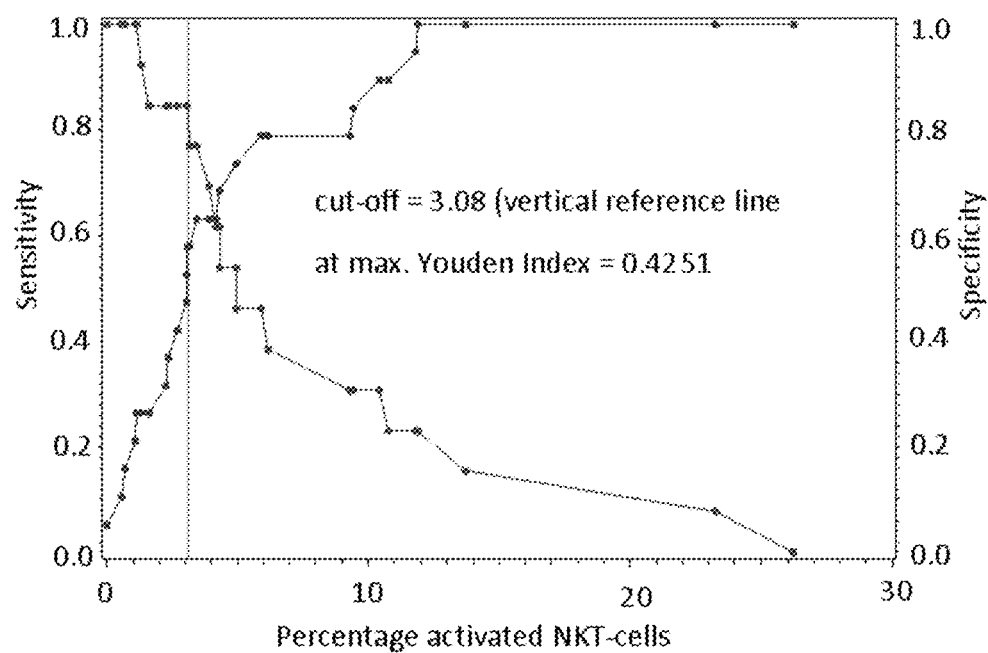
FIG. 2: Activated NKT cells versus sensitivity and specificity.

ROC curves in verum patients for activated NKT cells were established (FIG. 1). The area under the curve was determined to be 0.71, which is a clear indication of the reliability of the biomarker. The Youden-index, which can be used to determine an optimum cut-off value for the test's readout, shows an optimum at cut-off at 3.08% activated NKT cells. FIG. 2 shows activated NKT cells versus sensitivity and specificity.

All patients were now sorted into groups depending on their level of activated NKT cells. Patients with cell levels above the cut-off of 3.08% activated NKT cells were designated as biomarker positive, while patients with levels below the cut-off were labelled biomarker negative.

Figure 3A:
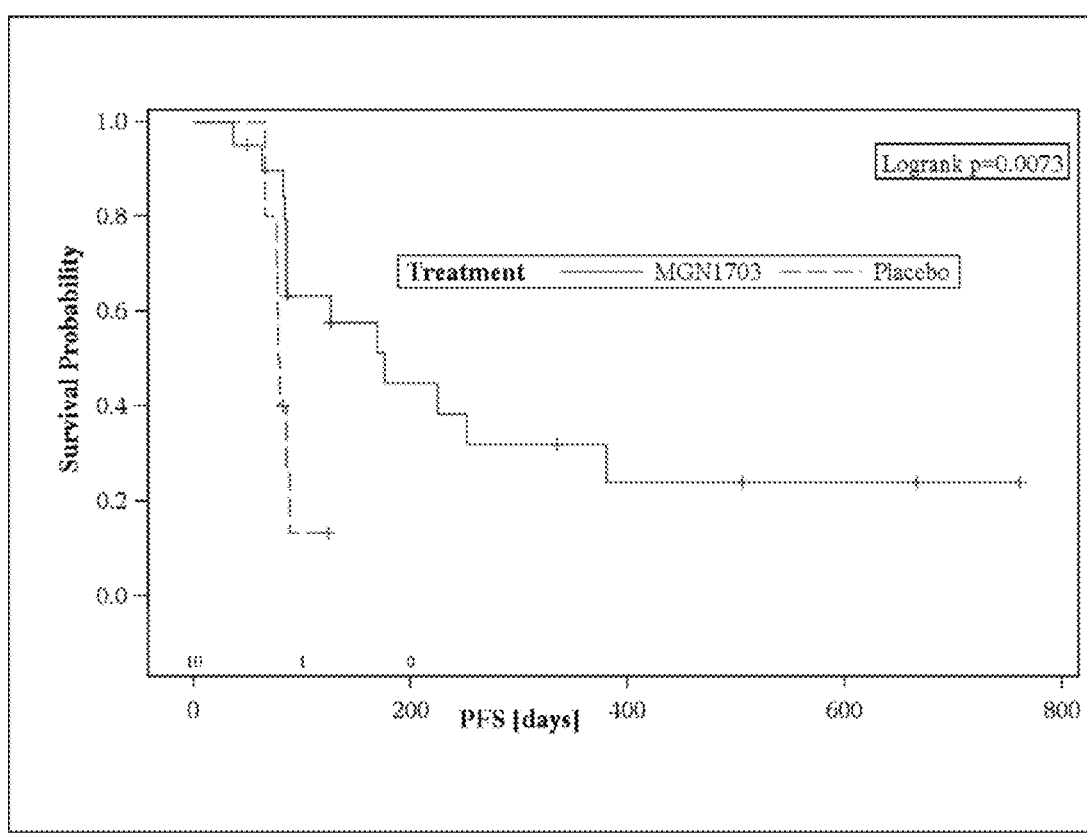
FIG. 3: a: Kaplan-Meier plot in biomarker positive patients for verum and placebo; b: Kaplan-Meier curve for the biomarker negative patients in both the verum and placebo arm.

FIG. 3a shows a Kaplan-Meier plot in biomarker positive patients for verum and placebo (solid line: patients treated with MGN1703; dotted line: patients treated with placebo). It is obvious that the survival probability within the biomarker positive group is surprisingly related to the application of the TLR-9 agonist.

Figure 3B:
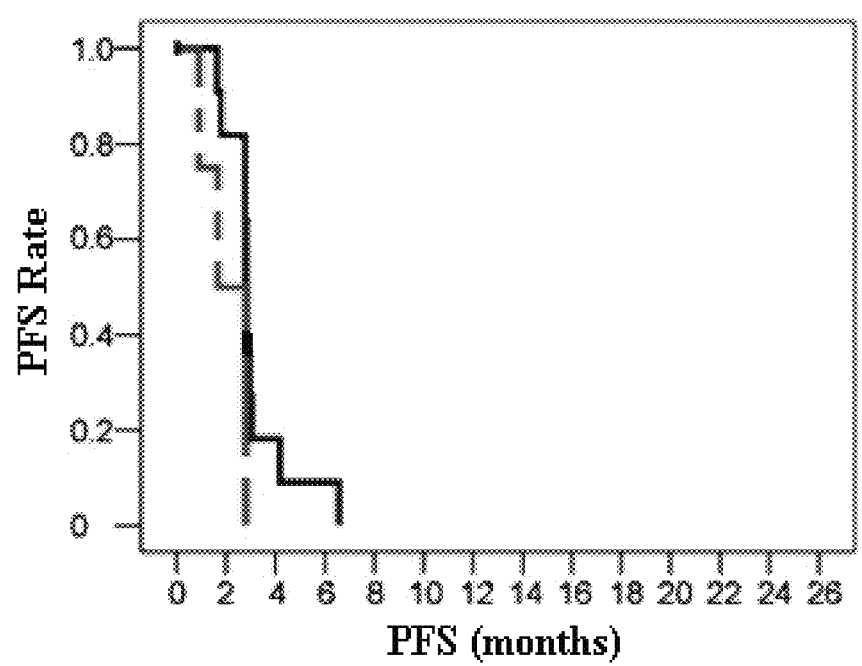

FIG. 3b shows a Kaplan-Meier curve for the biomarker negative patients in both the verum and placebo arm. It is obvious that the time of progression free survival is clearly shorter within this verum group as compared to the biomarker positive verum patients (comp. FIG. 3a).

Figure 4A:
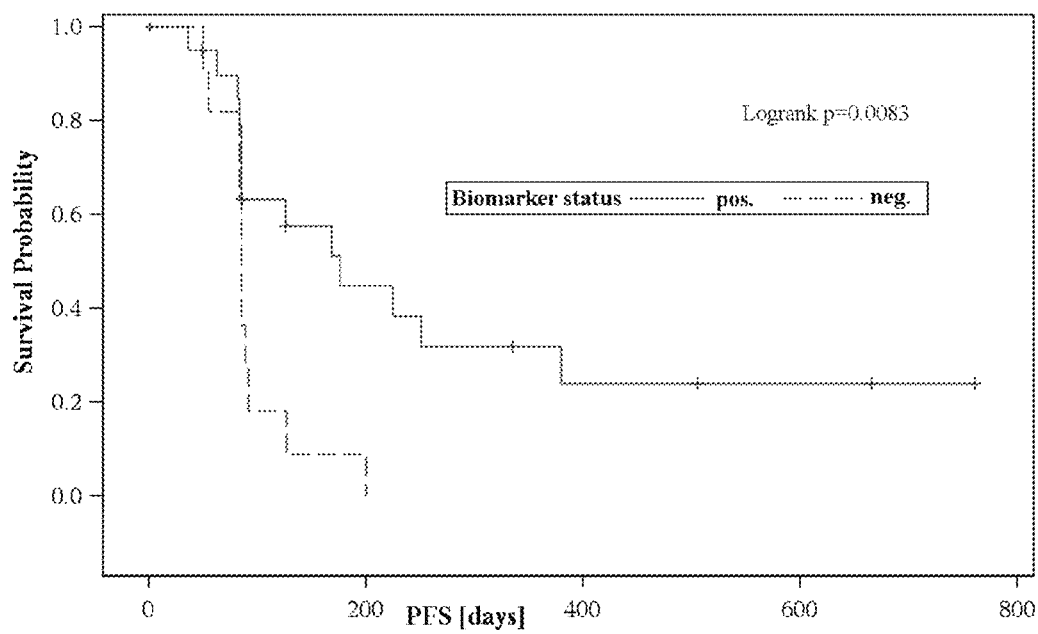
FIG. 4: a: Kaplan-Meier plot of biomarker positive patients versus biomarker negative patients in the verum arm; b: Kaplan-Meier plot of the placebo group for biomarker positive and negative patients.

FIG. 4a shows a Kaplan-Meier plot of biomarker positive patients versus biomarker negative patients, only from the verum treatment arm (solid line: biomarker positive patients; dotted line: biomarker negative patients). Clearly, the biomarker positive patients have a significant advantage in survival probability compared to the biomarker negative patients, even when both groups received the verum treatment MGN1703.

Figure 4B:
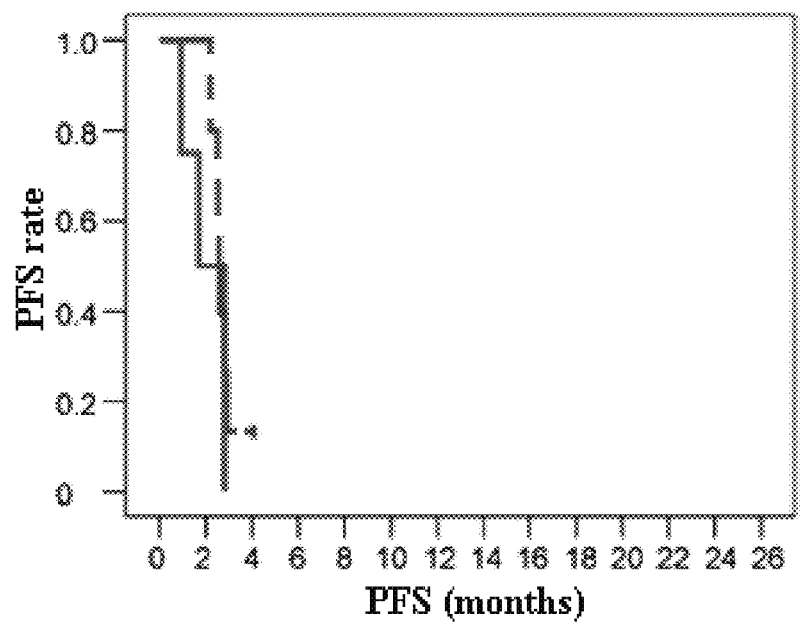

FIG. 4b shows a Kaplan-Meier plot of the placebo group for biomarker positive and negative patients (solid line: biomarker positive patients; dotted line: biomarker negative patients). It is obvious that both groups show a more or less identical progression free survival as they were only treated with placebo. Clearly, the biomarker is suitable for assessing whether a patient is a responder to the treatment with a TLR-9 agonist or not. Further, the placebo group shows that the biomarker is not related to effects caused by the overall health status of a patient.

The present invention provides new predictive biomarker for responder to a cancer treatment with a TLR-9 agonist, especially a covalently closed partially self-complementary DNA chain having a double stranded stem an single stranded terminal loops bearing unmethylated CG motifs. The determination of the frequencies of activated NKT cells (CD3+/CD56+/Cd69+) at baseline allows assessing the probability whether a patient is a responder to treatment with the DNA construct or not. Importantly, in the placebo arm, the patients with responder-like characteristics, behave the same way as non-responders did, showing that the prolonged progression-free survival time of the biomarker positive verum patients is in fact due to the applicability of the biomarkers for the selected therapy, not just a better overall health or any non-specific effect.

Material and Methods
Sample Handling

Whole blood (10 mL) for FACS was collected in Streck Cyto-Chex® BCT tubes. Within 2 hours after sampling the blood samples were shipped to the analytical laboratory. According to established Protocol, samples were stored at room temperature. The frequency and activation status of plasmacytoid dendritic cells (pDC), myeloid dendritic cells (mDC), monocytes, natural killer (NK) cells, NKT cells, B cells, T cells and other cell populations were evaluated.

Analytical Methods

Fluorescence activated cell sorting (FACS) were performed according to established principles. Whole blood samples were stained with fluorescence labeled antibodies and incubated. Phenotypical analysis of the immune cells was performed with a FACScalibur (Becton Dickinson) flow cytometer. Frequencies of the respective analyzed cell populations were documented for each sample of the patients.

Analysis of Human PBMC for the Activation of Specific Cell Populations

CD40 Expression of Plasmacytoid Dendritic Cells (pDC)

Cells were stained with the following combination of monoclonal antibodies: Anti-Lineage marker-FITC, (antibody cocktail containing antibodies directed against CD3, CD14, CD16, CD19, CD20, CD56); Anti-CD123-PE; Anti-HLA-DR-PerCP; Anti-CD40-APC; PDC were gated as: lineage negative, HLA-DR positive, CD123 positive cells. Within the PDC population CD40 was used as activation marker.

Activation of NK-, NK-T and T Cells Using the Activation Marker CD69

Cells were stained with the following combination of monoclonal antibodies: Anti CD3-FITC; Anti CD56-PE; Anti CD69-APC NK cells were gated as: CD3 negative, CD56 positive cells NK-T cells were gated as: CD3 positive, CD56 positive cells T cells were gated as: CD3 positive, CD56 negative CD69 was used as activation marker for all 3 populations.

CD86 Expression of Myeloid Dendritic Cells (MDC):

Cells were stained with the following combination of monoclonal antibodies: Anti-Lineage marker-FITC, (antibody cocktail containing antibodies directed against CD3, CD14, CD16, CD19, CD20, CD56); Anti-CD11c-PE; Anti-HLA-DR-PerCP; Anti-CD86-APC MDC were gated as: lineage negative, HLA-DR positive, CD11c positive cells.

Within the MDC population CD86 was used as activation marker.

CD86 Expression of B Cells and Monocytes; CD169 Expression of Monocytes

Cells were stained with the following combination of monoclonal antibodies: Anti CD14-FITC; Anti CD169-PE; Anti CD19-PerCP; Anti CD86-APC B cells were gated as CD19 positive cells. Within the B cell population CD86 was used as activation marker.

Monocytes were gated as CD14 positive cells. Within the monocyte population CD86 and CD169 were used as activation markers.

The invention claimed is:

1. A method for treating a patient suffering from cancer or an autoimmune disease with TLR-9 agonist MGN1703, wherein said method comprises:
taking a blood sample from a patient suffering from cancer or an autoimmune disease;
determining the frequency of activated natural killer T (NKT) cells of the blood sample of the patient;
predicting or monitoring whether the patient will respond or responds to the treatment with the TLR-9 agonist MGN1703, by evaluating whether the patient has a frequency of at least 3% of activated NKT cells of the whole NKT cell population; and administering, or continuing to administer, the TLR-9 agonist MGN1703 to a patient having a frequency of at least 3% of activated NKT cells of the whole NKT cell population.

2. The method of claim 1, wherein previously an induction therapy with a non-DNA drug was performed on the patient.

3. The method of claim 1, wherein said patient suffers from cancer.

4. The method of claim 3, wherein the TLR-9 agonist MGN1703 is part of a pharmaceutical composition.

5. The method of claim 4, wherein the pharmaceutical composition is a vaccine.

6. The method of claim 1, wherein the step of determining the frequency of activated natural killer T (NKT) cells of a blood sample of the patient comprises the steps of:
   staining the blood sample with fluorescence-labelled antibodies:
   Anti CD3-FITC,
   Anti CD56-PE,
   Anti CD69-APC;
   incubating the sample; and
   performing fluorescence activated cell sorting (FACS), wherein the activated NKT cells are gated as CD3 positive, CD56 positive and CD69 positive cells.

\* \* \* \* \*